(12) United States Patent
Zhou et al.

(10) Patent No.: US 9,456,842 B2
(45) Date of Patent: Oct. 4, 2016

(54) WIRE-GUIDED RECANALIZATION SYSTEM (71) Applicant: Boston Scientific Scimed, Inc., Maple Grove, MN (US)

(72) Inventors: Pu Zhou, Maple Grove, MN (US); Huisun Wang, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 177 days.

(21) Appl. No.: 13/940,854

(22) Filed: Jul. 12, 2013

(65) Prior Publication Data
US 2014/0018833 A1 Jan. 16, 2014

Related U.S. Application Data (60) Provisional application No. 61/671,326, filed on Jul. 13, 2012.

(51) Int. Cl.
*A61B 17/22* (2006.01)
*A61D 1/02* (2006.01)
(Continued)

(52) U.S. Cl.
CPC .. *A61B 17/320758* (2013.01); *A61M 25/0067* (2013.01); *A61M 25/0194* (2013.01); *A61B 2017/22039* (2013.01); *A61B 2017/22095* (2013.01); *A61B 2017/320766* (2013.01); *A61B 2090/0801* (2016.02); *A61B 2090/08021* (2016.02); *A61M 25/001* (2013.01); *A61M 25/003* (2013.01); *A61M 25/0108* (2013.01);
(Continued)

(58) Field of Classification Search
CPC .............. A61B 17/3207; A61B 2017/320758; A61B 17/320758; A61B 17/320783; A61B 17/32075; A61B 17/00234; A61B 17/32; A61B 17/32002; A61B 2017/22077; A61B 2017/320004; A61B 2017/22094; A61B 2017/22095; A61B 2017/22038; A61B 2017/22044; A61B 2017/00778; A61B 2017/320733; A61B 2017/320791; A61B 2017/1107; A61F 2/95; A61M 2025/0096; A61M 2025/0197
USPC ........ 606/159, 167–171, 84; 604/22, 27, 35, 604/508
See application file for complete search history.

(56) References Cited

U.S. PATENT DOCUMENTS 4,850,957 A * 7/1989 Summers ................. A61B 1/12 418/48
4,909,781 A * 3/1990 Husted ........... A61B 17/320758 604/22

(Continued)

FOREIGN PATENT DOCUMENTS

WO 2004078066 A2 9/2004
WO 2010049121 A2 5/2010

*Primary Examiner* — Katherine M Shi
*Assistant Examiner* — Mohamed Gabr
(74) *Attorney, Agent, or Firm* — Seager, Tufte & Wickhem LLP (57) ABSTRACT A recanalization catheter assembly for recanalization of an occluded blood vessel is disclosed. The recanalization catheter assembly includes an elongate shaft having a tubular portion, a guide member, and a rotary ablation tool. The tubular portion includes a distal opening, from where the rotary ablation tool extends distally. The guide member extends distal of the distal opening and includes a guidewire lumen to receive a guidewire therethrough. The guide member is configured to advance over the guidewire in a subintimal space between a first tissue layer and a second tissue layer of a wall of the blood vessel, while the rotary ablation tool is advanced in a true lumen of the blood vessel.

17 Claims, 5 Drawing Sheets

US 9,456,842 B2
Page 2

(51) Int. Cl.
*A61B 17/3207* (2006.01)
*A61M 25/00* (2006.01)
*A61M 25/01* (2006.01)

(52) U.S. Cl.
CPC .......... *A61M 2025/0046* (2013.01); *A61M 2025/0183* (2013.01); *A61M 2025/0197* (2013.01)

(56) References Cited

U.S. PATENT DOCUMENTS

| | | | |
|---|---|---|---|
| 5,087,265 A * | 2/1992 | Summers | A61B 17/320758 604/22 |
| 5,312,427 A * | 5/1994 | Shturman | A61B 17/3207 606/159 |
| 5,431,673 A * | 7/1995 | Summers | A61B 17/320758 606/167 |
| 5,830,222 A * | 11/1998 | Makower | A61B 1/3137 604/99.03 |
| 5,925,055 A * | 7/1999 | Adrian | A61B 17/22012 604/22 |
| 5,935,108 A * | 8/1999 | Katoh | A61B 17/3207 604/164.11 |
| 5,938,671 A * | 8/1999 | Katoh | A61B 17/3207 606/159 |
| 5,968,064 A | 10/1999 | Selmon et al. | |
| 6,010,449 A * | 1/2000 | Selmon | A61B 5/0084 600/104 |
| 6,027,460 A * | 2/2000 | Shturman | A61M 25/0133 600/129 |
| 6,068,638 A | 5/2000 | Makower | |
| 6,096,054 A * | 8/2000 | Wyzgala | A61B 17/320725 606/170 |
| 6,113,615 A * | 9/2000 | Wulfman | A61B 17/320758 606/159 |
| 6,120,516 A | 9/2000 | Selmon et al. | |
| 6,146,395 A * | 11/2000 | Kanz | A61B 17/320725 606/159 |
| 6,159,225 A | 12/2000 | Makower | |
| 6,190,353 B1 | 2/2001 | Makower et al. | |
| 6,217,527 B1 | 4/2001 | Selmon et al. | |
| 6,217,549 B1 | 4/2001 | Selmon et al. | |
| 6,221,049 B1 | 4/2001 | Selmon et al. | |
| 6,231,546 B1 | 5/2001 | Milo et al. | |
| 6,231,587 B1 | 5/2001 | Makower | |
| 6,235,000 B1 | 5/2001 | Milo et al. | |
| 6,241,667 B1 | 6/2001 | Vetter et al. | |
| 6,398,798 B2 | 6/2002 | Selmon et al. | |
| 6,428,551 B1 * | 8/2002 | Hall | A61B 17/320758 128/899 |
| 6,451,036 B1 * | 9/2002 | Heitzmann | A61B 17/320758 606/159 |
| 6,506,178 B1 * | 1/2003 | Schubart | A61B 17/00234 604/93.01 |
| 6,508,825 B1 * | 1/2003 | Selmon | A61M 29/02 604/104 |
| 6,511,458 B2 | 1/2003 | Milo et al. | |
| 6,514,217 B1 | 2/2003 | Selmon et al. | |
| 6,579,302 B2 | 6/2003 | Duerig et al. | |
| 6,599,304 B1 | 7/2003 | Selmon et al. | |
| 6,638,247 B1 | 10/2003 | Selmon et al. | |
| 6,663,577 B2 * | 12/2003 | Jen | A61B 17/3207 600/585 |
| 6,719,725 B2 | 4/2004 | Milo et al. | |
| 6,955,175 B2 | 10/2005 | Stevens et al. | |
| 7,004,173 B2 | 2/2006 | Sparks et al. | |
| 7,179,270 B2 | 2/2007 | Makower | |
| 7,229,421 B2 | 6/2007 | Jen et al. | |
| 7,357,794 B2 | 4/2008 | Makower et al. | |
| 7,740,623 B2 | 6/2010 | Nayak et al. | |
| 7,918,859 B2 | 4/2011 | Katoh et al. | |
| 7,918,870 B2 | 4/2011 | Kugler et al. | |
| 7,938,819 B2 | 5/2011 | Kugler et al. | |
| 8,025,655 B2 | 9/2011 | Kugler et al. | |
| 8,083,727 B2 | 12/2011 | Kugler et al. | |
| 9,101,387 B2 * | 8/2015 | Plowe | A61B 17/320758 |
| 2001/0000041 A1 | 3/2001 | Selmon et al. | |
| 2001/0012924 A1 | 8/2001 | Milo et al. | |
| 2002/0029052 A1 * | 3/2002 | Evans | A61B 17/22 606/159 |
| 2002/0103459 A1 * | 8/2002 | Sparks | A61B 17/3207 604/164.13 |
| 2002/0128677 A1 | 9/2002 | Duerig et al. | |
| 2003/0120195 A1 | 6/2003 | Milo et al. | |
| 2003/0139763 A1 | 7/2003 | Duerig et al. | |
| 2004/0167554 A1 * | 8/2004 | Simpson | A61B 17/320758 606/159 |
| 2004/0215186 A1 * | 10/2004 | Cornelius | A61B 18/1492 606/41 |
| 2004/0230219 A1 | 11/2004 | Roucher, Jr. | |
| 2004/0254597 A1 * | 12/2004 | Schwartz | A61B 17/3207 606/167 |
| 2005/0171478 A1 | 8/2005 | Selmon et al. | |
| 2006/0094930 A1 | 5/2006 | Sparks et al. | |
| 2006/0184011 A1 | 8/2006 | Macaulay et al. | |
| 2006/0217751 A1 * | 9/2006 | O'Quinn | A61B 17/32002 606/180 |
| 2006/0276749 A1 * | 12/2006 | Selmon | A61B 6/12 604/164.01 |
| 2007/0010840 A1 * | 1/2007 | Rosenthal | A61B 17/3207 606/170 |
| 2007/0060936 A1 * | 3/2007 | Benavitz | A61B 17/1633 606/180 |
| 2007/0093779 A1 | 4/2007 | Kugler et al. | |
| 2007/0093780 A1 | 4/2007 | Kugler et al. | |
| 2007/0093781 A1 | 4/2007 | Kugler et al. | |
| 2007/0093782 A1 | 4/2007 | Kugler et al. | |
| 2007/0129740 A1 * | 6/2007 | Schwartz et al. | 606/159 |
| 2007/0208368 A1 | 9/2007 | Katoh et al. | |
| 2007/0265596 A1 | 11/2007 | Jen et al. | |
| 2007/0276419 A1 * | 11/2007 | Rosenthal | A61B 17/32002 606/159 |
| 2008/0033423 A1 | 2/2008 | Peacock | |
| 2008/0065125 A1 * | 3/2008 | Olson | A61B 17/320758 606/159 |
| 2008/0125748 A1 | 5/2008 | Patel | |
| 2008/0154172 A1 | 6/2008 | Mauch | |
| 2008/0161841 A1 * | 7/2008 | Clague | A61B 17/00008 606/159 |
| 2008/0200896 A1 | 8/2008 | Shmulewitz et al. | |
| 2008/0228171 A1 | 9/2008 | Kugler et al. | |
| 2008/0243065 A1 | 10/2008 | Rottenberg et al. | |
| 2008/0243067 A1 | 10/2008 | Rottenberg et al. | |
| 2008/0249397 A1 | 10/2008 | Kapadia | |
| 2009/0005755 A1 | 1/2009 | Keith et al. | |
| 2009/0088685 A1 | 4/2009 | Kugler et al. | |
| 2009/0093791 A1 * | 4/2009 | Heuser | A61B 17/12136 604/509 |
| 2009/0124899 A1 | 5/2009 | Jacobs et al. | |
| 2009/0209910 A1 * | 8/2009 | Kugler | A61B 17/11 604/103.1 |
| 2009/0254107 A1 * | 10/2009 | Katoh | A61M 25/0012 606/159 |
| 2009/0264826 A1 | 10/2009 | Thompson | |
| 2009/0292296 A1 | 11/2009 | Pansky et al. | |
| 2009/0299171 A1 | 12/2009 | Duffy et al. | |
| 2009/0299402 A1 | 12/2009 | Orihashi et al. | |
| 2010/0004730 A1 * | 1/2010 | Benjamin | A61F 2/95 623/1.11 |
| 2010/0023033 A1 * | 1/2010 | Mauch | A61B 17/22 606/159 |
| 2010/0063534 A1 | 3/2010 | Kugler et al. | |
| 2010/0069945 A1 | 3/2010 | Olson et al. | |
| 2010/0125244 A1 | 5/2010 | McAndrew | |
| 2010/0125253 A1 * | 5/2010 | Olson | A61B 17/320758 604/267 |
| 2010/0317973 A1 | 12/2010 | Nita | |
| 2011/0054503 A1 * | 3/2011 | Rizk | A61B 17/3207 606/159 |
| 2011/0112564 A1 | 5/2011 | Wolf | |
| 2011/0144677 A1 | 6/2011 | Ward et al. | |
| 2011/0166591 A1 | 7/2011 | Katoh et al. | |

(56) References Cited

U.S. PATENT DOCUMENTS

| | | | | |
|---|---|---|---|---|
| 2012/0035633 A1* | 2/2012 | Shturman | ...... | A61B 17/320758 606/159 |
| 2013/0066345 A1* | 3/2013 | Wilkinson | ..... | A61B 17/320725 606/159 |
| 2013/0072957 A1* | 3/2013 | Anderson | ........... | A61M 25/104 606/194 |
| 2013/0110144 A1* | 5/2013 | Olson | .................... | A61B 17/11 606/159 |
| 2015/0342629 A1* | 12/2015 | Schneider | ............ | A61B 18/245 606/7 |

* cited by examiner

WIRE-GUIDED RECANALIZATION SYSTEM

CROSS-REFERENCE TO RELATED APPLICATION

This application claims the benefit of U.S. Provisional Application Ser. No. 61/671,326, filed Jul. 13, 2012, the entire disclosure of which is incorporated herein by reference.

TECHNICAL FIELD

This disclosure relates to systems and methods for recanalization of an occluded blood vessel. More particularly, the technologies disclosed herein relate to systems and methods for wire-guided recanalization of the occluded blood vessel.

BACKGROUND

A chronic total occlusion (CTO) is an arterial vessel blockage that obstructs blood flow through a vessel. A CTO generally results from a diseased condition called arthrosclerosis which can occur in both coronary and peripheral arteries. In some instances, it may be difficult or impossible to penetrate the CTO with a medical device in an antegrade direction to recanalize the vessel. Accordingly, techniques have been developed for creating a subintimal pathway (a path between the intimal and adventitial tissue layers of the vessel wall) around the occlusion and then reentering the true lumen of the vessel distal of the occlusion. In some instances, reentering the true lumen from the subintimal space and/or recanalization pathway may be difficult. Accordingly, it is desirable to provide alternative recanalization devices and/or methods having improved mechanisms for recanalization of a blood vessel in which an occlusion, such as a CTO, is present.

SUMMARY

The disclosure is directed to several alternative designs, and methods of using medical device structures and assemblies for performing recanalization of occluded blood vessels.

Accordingly, one illustrative embodiment is a recanalization catheter assembly for recanalization of a blood vessel having an occlusion therein. The recanalization catheter assembly includes an elongate catheter shaft, a guide member, and a rotary ablation tool. The elongate shaft includes a tubular portion, which includes a distal opening. The guide member extends distal of the distal opening and includes a guidewire lumen for receiving a guidewire therethrough. The rotary ablation tool extends distally from the distal opening alongside the guide member. The guide member is configured to be advanced over the guidewire in a subintimal space between a first tissue layer and a second tissue layer of a wall of the blood vessel, while the rotary ablation tool is advanced in a true lumen of the blood vessel to ablate the occlusion.

Another illustrative embodiment of the recanalization catheter assembly, discussed above, may additionally include a cutter secured to the elongate catheter shaft proximal of the rotary ablation tool and distal to the distal opening. The cutter is configured to cut through the first tissue layer between the guide member and the rotary ablation tool when the rotary ablation tool is advanced distally through the occlusion.

The above summary of some example embodiments is not intended to describe each disclosed embodiment or every implementation of the present disclosure.

BRIEF DESCRIPTION OF THE DRAWINGS

The disclosure may be more completely understood in consideration of the following detailed description of various embodiments in connection with the accompanying drawings, in which.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification. All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

While the devices and methods described herein are discussed relative to recanalization of blood vessels blocked by a CTO, it is contemplated that the devices and methods may be used in other applications where recanalization of an occluded blood vessel is desired.

The present disclosure provides methods and systems for recanalization of an occluded blood vessel. The system may include an elongate shaft having a tubular portion with a distal opening. A guide member and a rotary ablation tool may extend distal of the distal opening alongside each other, such that the rotary ablation tool extends distally from the distal opening beside the guide member. The rotary ablation tool may progress in a true lumen of an occluded blood vessel simultaneous to the distal movement of the guide member being advanced through a subintimal space of the blood vessel between tissue layers of the wall of the blood vessel. The guide member, configured to advance over a guidewire positioned in the subintimal space, may stabilize the rotary ablation tool in the true lumen and prevent deflection of the rotary ablation tool as the rotary ablation tool advances through the occlusion in the blood vessel. In some instances, the guidewire may not need to re-enter the true lumen of the blood vessel distal of the occlusion from the subintimal space, thus obviating a need of a subintimal re-entry device.

Figure 1:
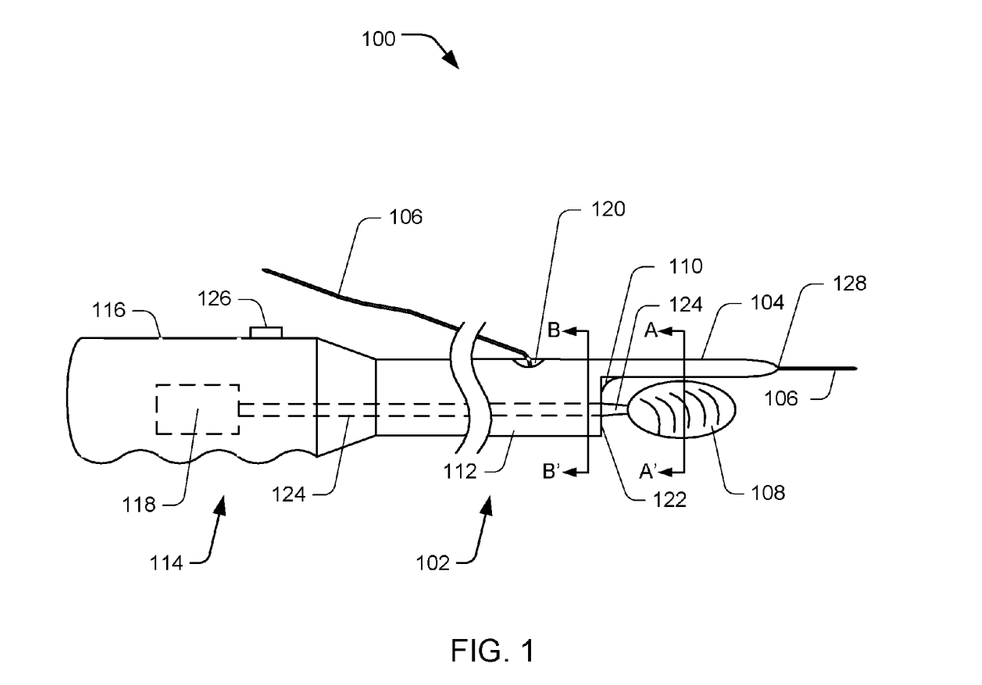
FIG. 1 is a side view of an exemplary recanalization catheter assembly.

FIG. 1 is a side view of an exemplary recanalization catheter assembly 100 for recanalization of a blood vessel. In one embodiment, the recanalization catheter assembly 100 may include an elongated catheter shaft 102, an elongated guide member 104, a rotary ablation tool 108, and a cutter 110. The recanalization catheter assembly may be advanceable over a guidewire 106 to reach a remote location in a vasculature. The catheter shaft 102 may include a flexible tubular portion 112 extending from a distal end of a handle assembly 114, which may include one or more components. For example, the handle assembly 114 may include an ergonomically designed handle 116 to provide a comfortable grip on the recanalization catheter assembly 100 during operation, and one or more actuation means to control its operation. The handle assembly 114 may also include a motor 118 to control the operation of the rotary ablation tool 108. Also, the handle assembly 114 may include one or more ports or openings (not shown in the figure) for a variety of purposes, for example, to host the guidewire, to insert medical devices, for fluid delivery and/or aspiration, to provide electrical pathways, etc.

The tubular portion 112 may be configured with a substantially circular cross-section, though other suitable cross-sectional shapes of the tubular portion 112 may be employed, such as elliptical, oval, polygonal, irregular, etc. In addition, the tubular portion 112 may be flexible along its entire length or adapted for flexure along portions of its length to navigate through a tortuous vasculature. The required degree of flexibility of the tubular portion 112 may be predetermined based on its intended navigation to a target vascular passage and the amount of inertial force required for advancing the tubular portion 112 through the vascular passage. The cross-sectional dimensions and/or length of the tubular portion 112 may vary according to the desired application to provide access to a desired location in the vasculature. In some instances, a 6 F or a 5 F catheter may be used as the tubular portion 112, where 'F', also known as French catheter scale, is a unit to measure catheter diameter (1 F=⅓ mm). In addition, the tubular portion 112 or a portion thereof may be selectively steerable. Mechanisms such as, pull wires or other actuators may be used to selectively steer the tubular portion 112.

The tubular portion 112 may include a proximal port 120, which may be located anywhere along the length of the tubular portion 112. This port 120 may be used to introduce the guidewire 106 of appropriate thickness into the tubular portion 112. The distal end of the tubular portion 112 may include a distal opening 122, sized as discussed below. It will be understood that the tubular portion 112 may be further adapted to include more openings or lumens, which may be configured for a variety of purposes such as delivering medical devices, providing fluids, such as saline, to a target location, aspiration of fluid and/or tissue from the treatment site, etc.

Guidewire 106 may be a wire on which the tubular portion 112 may be configured to advance for delivery to a remote distal location. The guidewire 106 may be a metallic or polymeric wire, formed of stainless steel or nitinol, for example. The dimensions of guidewire 106 may depend on the application of the guidewire 106. For example, the length of the guidewire 106 may depend on the length of the tubular portion 112 and the guide member 104, the target location within the anatomy, and the extent to which the guidewire 106 may need to extend distally beyond the guide member 104. The diameter of the guidewire 106 may be selected such that the guidewire 106 may be slidably received in the guidewire lumens associated with the tubular portion 112 and the guide member 104. In some embodiments, the guidewire 106 may have a diameter ranging from about 0.014 inches to about 0.035 inches, for example.

Guide member 104 may extend distally from the upper rim of tubular portion 112 or at a different location, if desired. In some instances, the guide member 104 may be generally spatulate or arcuate in form. At its proximal end, where the guide member 104 joins the tubular portion 112, radius of the guide member 104 may match the radius of tubular portion 112, extending around the rim about 90°-180°, or about 100°-135°, in some instances. In some embodiments, the guide member 104 may taper distally to a blunt tip. A guidewire lumen 202, shown in FIG. 2, may extend through the length of guide member 104, or a portion thereof.

The guide member 104 may be detachably connected, permanently secured to, or formed as an integral component of the tubular portion 112. The guide member 104 may be coupled to the distal end of the tubular portion 112 by any suitable coupling mechanism, such as assemblies joined by welding, molding, adhesive bonding, thermal bonding, a snap fit, screw fit, or other known attachment mechanisms capable of achieving the intended purpose in the intended environment. Suitable permanent securement methods may include, but are not limited to, adhesive bonding, thermal bonding, molding or welding, depending on the material of the guide member 104 and/or the tubular portion 112. In some instances, the guide member 104 may be formed integral with the distal end of the tubular portion 112.

In some embodiments, the guide member 104 and the catheter shaft 102 including the tubular portion 112 may be coated with a suitable low-friction material, such as polytetrafluoroethylene (PTFE), such as TEFLON®, polyetheretherketone (PEEK), polyimide, nylon, polyethylene, silicone, hydrophilic, or other lubricious polymer coatings, to reduce surface friction.

Additionally, the tubular portion 112 and/or the guide member 104 may be provided with one or more radiopaque markers (not shown in the figure) to facilitate locating the precise position of the tubular portion 112, the guide member 104, the rotary ablation tool 108 and/or the distal opening 122 for example, as well as their orientation, within the vessel wall using fluoroscopy or other imaging techniques during a medical procedure. In some instances, a radiopaque marker may be located proximate to the distal end of the tubular portion 112 and/or proximate to the distal end of the guide member 104. The radiopaque marker(s) may be formed of any biocompatible polymeric material and/or metallic material providing a distinct image. For example, the radiopaque marker(s) may be formed of a metal construct (e.g. a ring or band) such as tungsten, platinum or a platinum-chromium alloy, molybdenum or a molybdenum alloy, or a polymer having a radiopaque filler dispersed therein. For example, the radiopaque marker(s) may be made of a suitable biocompatible polymeric material, such as polyurethane material, that may be impregnated with, or otherwise include, one or more radiopaque materials, such as metal, metal flakes, metal powder, ceramics, ceramics powder, barium sulfate ($BaSO_4$), bismuth subcarbonate ($Bi_2O_2(CO_3)$), bismuth trioxide ($Bi_2O_3$), or any other suitable radiopaque material. The marker(s) may be secured to the tubular portion 112 and/or the guide member 104 utilizing a variety of methods including adhesive bonding, crimping, thermal bonding, or any other suitable means.

Rotary ablation tool 108 may be any cutting, boring or drilling device configured for introduction into a vascular passage and boring through obstructions such as an occlusion (e.g., a CTO). For example, the rotary ablation tool 108 may be a diamond-etched drilling device, substantially oval in longitudinal cross-section. Other suitable devices include, but are not limited to, enhanced wire tip drilling devices, angled drilling devices, micro drilling devices, and expandable drilling devices. In some embodiments, the ablation device may be an electrosurgical (e.g., radio frequency) ablation device, ultrasonic ablation device, laser ablation device, or other ablation device, if desired. A drive shaft 124 may extend from the proximal end of the rotary ablation tool 108 to the motor 118 in the handle assembly 114. This shaft 124 may be flexible and adapted to drive the rotary ablation tool 108, such as by rotational motion. Motor 118 may be further attached to a power source and may be provided with a suitable actuation mechanism, such as switch 126 to activate and/or deactivate the motor 118, and thus rotational movement of the ablation tool 108. As seen in FIG. 1, distal opening 122 may be sized to receive rotary ablation tool 108 and/or drive shaft 124 of rotary ablation tool 108. In some embodiments, the rotary ablation tool 108 may be positioned within the distal opening 122 while being advanced to the treatment site (e.g., occlusion). Once at the treatment site, an actuating member (not shown) may be actuated to advance the rotary ablation tool 108 out of distal opening 122 into an operating configuration as shown in FIG. 1. In other embodiments, the rotary ablation tool 108 may be positioned in an operating configuration, extending from the distal opening 122, while being advanced to the treatment site. In other embodiments, the rotary ablation tool 108 may be advanced through the lumen of the tubular portion 112 of the elongate shaft 102 subsequent to positioning the distal opening 122 of the tubular portion 112 proximate the treatment site. In an operating configuration, the distal end of rotary ablation tool 108 may extend distally beyond the distal tip of tubular portion 112, such that the rotary ablation tool 108 may engage the occlusion as the rotary ablation tool 108 is advanced distally. Guide member 104 may extend distal of the distal opening 122 and the distal tip, and may extend along at least a portion of the rotary ablation tool 108 extending from the tubular portion 112. In some instances, the distal tip of the guide member 104 may extend to the distal tip of the rotary ablation tool 108, or distally beyond the distal tip of the rotary ablation tool 108.

A cutter 110, which, in some instances, may have the form of a sharpened blade, may be mounted a distal portion of the catheter shaft 102, such as on a proximal end portion of guide member 104 at the distal end of the tubular portion 112, or at another location, if desired. The cutter 110 may be adapted to have a variety of shapes, for example, those similar to wedge, crescent, concave, convex, etc., and may be engineered to have different sizes relative to a desired spacing between the guide member 104 and the rotary ablation tool 108. For example, a cutter 110 having a sharp edge may be placed at the junction of the guide member 104 and the tubular portion 112 to dissect a tissue layer, such as an intimal layer, passing between the guide member 104 and the rotary ablation tool 108 as the rotary ablation tool 108 is advanced distally through an occlusion in a blood vessel while the guide member 104 is advanced distally through a subintimal space between the intimal layer and the adventitial layer of the vessel wall.

Recanalization catheter assembly 100 may be configured to advance over the guidewire 106 for delivery to a remote location in the vasculature of a patient. Guidewire 106 may be advanced through the patient's vasculature to the remote location to provide a pathway over which the catheter shaft 102 may be subsequently advanced to the treatment site. For example, the guidewire 106 may be received through a guidewire lumen extending through the guide member 104, such that the guide member 104 advances over the guidewire 106. To accomplish the task of delivering the recanalization catheter assembly 100 in the vasculature, any of several device configurations may be employed. For example, in some instances the catheter shaft 102 may be configured as a single-operator-exchange (SOE) catheter having a guidewire lumen extending from an exit opening 128 at the distal end of the guide member 104 to a proximal port 120 located in the tubular portion 112 distal of the handle assembly 114. In other embodiments, the guide member 104 may be adapted to include a guidewire lumen extending through the entire length of the guide member 104 and continues through the tubular portion 112 of the catheter shaft 102. The guidewire lumen may extend from the exit opening 128 to a proximal opening (not shown in the figure) located at a proximal end of the catheter shaft 102. The tubular portion 112 along with the drive shaft 124, the rotary ablation tool 108, and the cutter 110 may be configured to collectively and simultaneously advance in the blood vessel as the guide member 104 progresses distally over the guidewire 106. However, in other embodiments, the rotary ablation tool 108 may be configured to be advanced distally through a lumen of the elongate shaft 102 subsequent advancing the elongate shaft 102 to the treatment site with the guide member 104 tracking over the guidewire 106.

The various components of the recanalization catheter assembly 100 may be formed of any biocompatible materials, as desired. For example, in some embodiments, the tubular portion 112, the guide member 104, and the drive shaft 124, or portions thereof, may be made of a variety of metallic materials, including stainless steel and nickel-titanium alloy such as nitinol, a variety of polymeric materials such as polyamide, polyether block amide, polyethylene, or polyethylene terephthalate, or a combination of metallic and polymeric materials. Further, the cutter 110 may be made of a variety of metallic materials, ceramic materials, or polymeric materials known in the art, including those discussed above.

Figure 2:
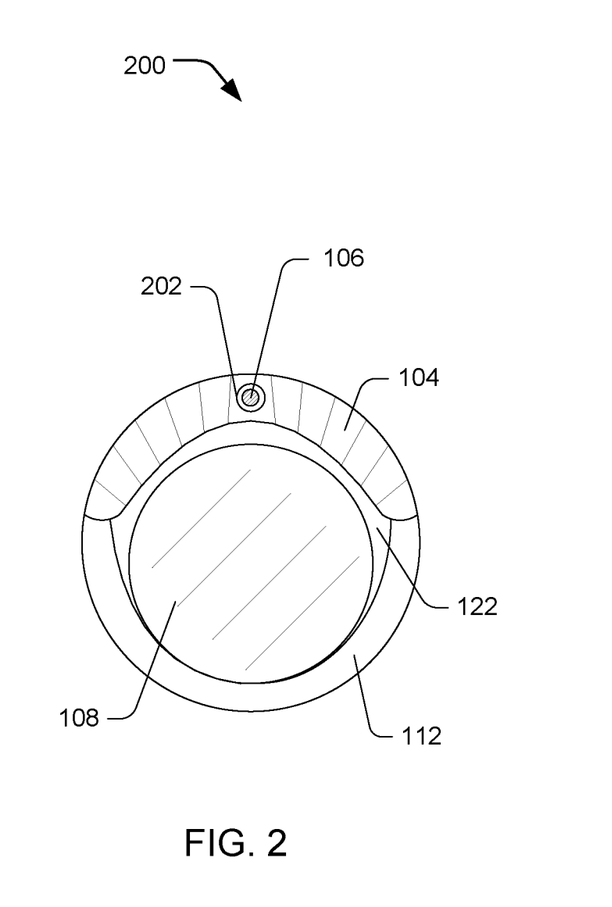
FIG. 2 is a cross-sectional view of the exemplary recanalization catheter assembly of FIG. 1 taken along plane A-A' of FIG. 1.

FIG. 2 is a cross-sectional view 200 of the exemplary recanalization catheter assembly of FIG. 1 taken along plane A-A' of FIG. 1. As shown, the recanalization catheter assembly 100 may include the tubular portion 112 having predetermined dimensions adapted for introduction into a vascular passage. The tubular portion 112 may include a distal opening 122, adjacent to the proximal end of guide member 104, with the guide member 104 extending distally from the upper portion of the tubular portion 112 at the distal opening 122, as discussed above. A guidewire lumen 202 may extend through the length of guide member 104 and be configured to receive the guidewire 106 therethrough. In some instances, the guide member 104 may function to protect guidewire 106 from being damaged by the rotary ablation tool 108 and/or interfering with use of the rotary ablation tool 108. The guidewire lumen 202 may have a diameter of about 0.015 inches to 0.050 inches, for example. Rotary ablation tool 108 may generally be aligned with the central axis of the tubular portion 112, or offset from the central axis of the tubular portion 112, if desired.

Figure 3:
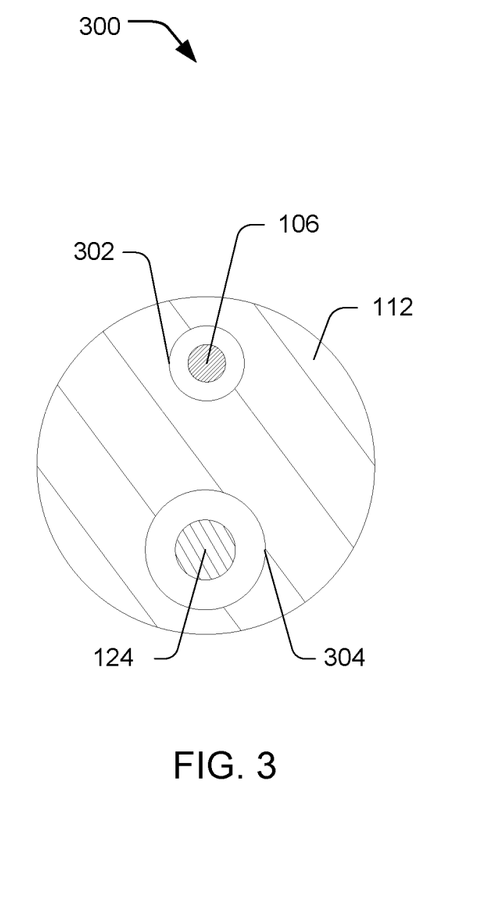
FIG. 3 is a cross-sectional view of the exemplary recanalization catheter assembly of FIG. 1 taken along plane B-B' of FIG. 1.

FIG. 3 illustrates a cross-sectional view 300 of the exemplary recanalization catheter assembly of FIG. 1 taken along B-B' of FIG. 1. As shown in FIG. 3, the tubular portion 112 may include a guidewire lumen 302 and a drive shaft lumen 304. Guidewire lumen 302 may be aligned with or otherwise connected to the guidewire lumen 202 of the guide member 104 and may extend through a length of tubular portion 112 to the open proximal port 120, for example. The flexible drive shaft 124 may extend distally from motor 118 located within the handle 116, through the drive shaft lumen 304 to the rotary ablation tool 108 to provide rotational motion to the rotary ablation tool 108. Apart from lumens 302, 304, the tubular portion 112 may be of solid material as shown in the illustrated embodiment, or the tubular portion 112 may have another configuration. Those of skill in the art will understand that other lumens, carrying a variety of medical devices, providing fluid pathways, and/or providing pathways for various other wires or structures, could be formed in tubular portion 112 along with those illustrated, if desired.

FIGS. 4A-4D illustrate aspects of an exemplary method for recanalization of an occluded blood vessel using the recanalization catheter assembly of FIG. 1. The figures show a cross-section 400 of a blood vessel, which typically includes three tissue layers, namely, an innermost layer or intimal layer 402 (i.e., tunica intima), an intermediate layer or media layer 404 (i.e., tunica media), and an outermost layer or adventitial layer 406 (i.e., tunica adventitia). The intimal layer 402 is a layer of endothelial cells lining the lumen of the vessel, as well as a sub-endothelial layer made up of mostly loose connective tissue. The media layer 404 is a muscular layer formed primarily of circumferentially arranged smooth muscle cells. The adventitial layer 406, which forms the exterior layer of the vessel wall, is formed primarily of loose connective tissue made up of fibroblasts and associated collagen fibers.

In some instances of vascular total occlusion, it may be difficult to pass through an occlusion, such as a total chronic occlusion (CTO) in a true lumen 408 of the blood vessel with a medical device to recanalize the vessel. FIGS. 4A-4D illustrate one possible approach to recanalizing a blood vessel by creating a passageway through the occlusion with an ablation device in the true lumen while being guided by a subintimally positioned guidewire positioned between tissue layers of the wall of the blood vessel adjacent to the occlusion.

Figure 4A:
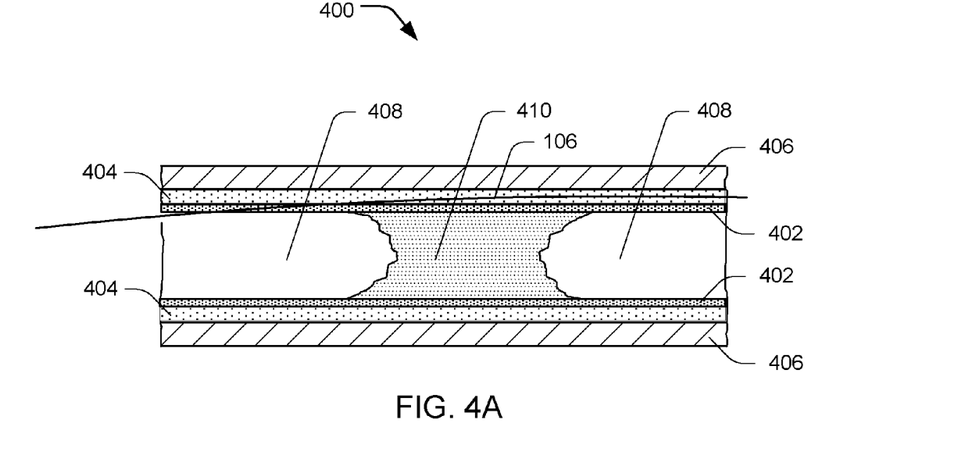
FIGS. 4A-4D illustrate aspects of an exemplary method for recanalizing an occluded blood vessel using the recanalization catheter assembly of FIG. 1.

As shown in FIG. 4A, a guidewire 106 may initially be advanced through the true lumen 408 of the vessel to a location proximate to a proximal end of an occlusion 410. The guidewire 106 may then be manipulated to penetrate into the vessel wall to create a subintimal space between the intimal layer 402 and the adventitial layer 406 from a location proximal of the proximal end of the occlusion 410. This subintimal space may be created in the media layer 404, for example. With the tip of the guidewire 106 located between the intimal layer 402 and the adventitial layer 406, the guidewire 106 may be further advanced distally within the vessel wall until the distal tip of the guidewire 106 is located distal of the distal end of the occlusion 410, forming a subintimal space from proximal of the occlusion 410 to a location distal of the occlusion 410. In some instances, the guidewire 106 may not need to re-enter the true lumen 408 of the blood vessel distal of the occlusion 410 from the subintimal space, thus obviating a need of a subintimal re-entry device. Accordingly, the distal tip of the guidewire 106 may be located within the subintimal space between tissue layers of the wall of the vessel throughout the ablation procedure.

Figure 4B:
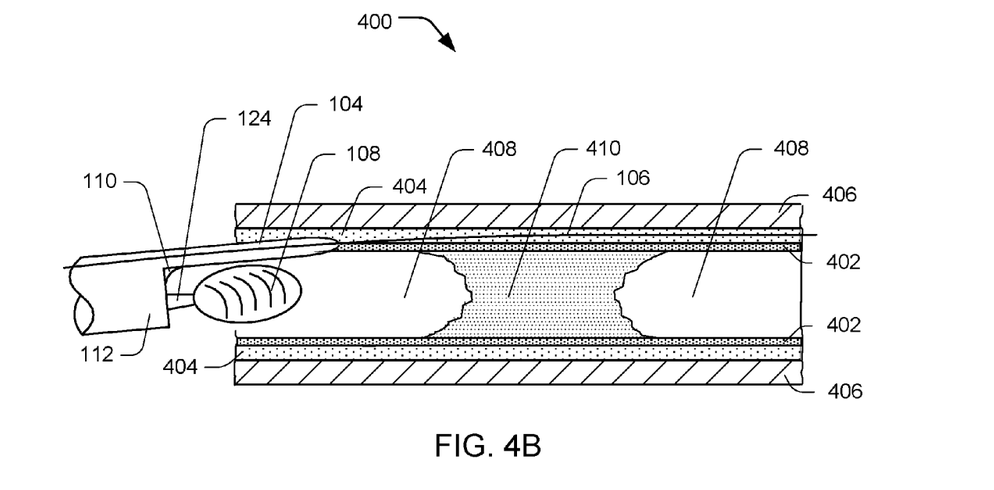

As shown in FIG. 4B, with the guidewire 106 advanced into the subintimal space adjacent to the occlusion 410, the recanalization catheter assembly 100 may be advanced over guidewire 106 to the point where guidewire 106 exits the true lumen 408 and passes through the intimal layer 402 into the wall of the vessel, immediately proximal of the occlusion 410. For example, the guide member 104 may be advanced over the guidewire 106, with the guidewire 106 passing through the guidewire lumen 202. The guide member 104 may be configured to follow the guidewire 106 and advance into the subintimal space between the intimal layer 402 and the adventitial layer 406, while the rotary ablation tool 108 and the tubular portion 112, hereinafter collectively referred to as the catheter sub-unit, are advanced in the true lumen 408 of the blood vessel.

Figure 4C:
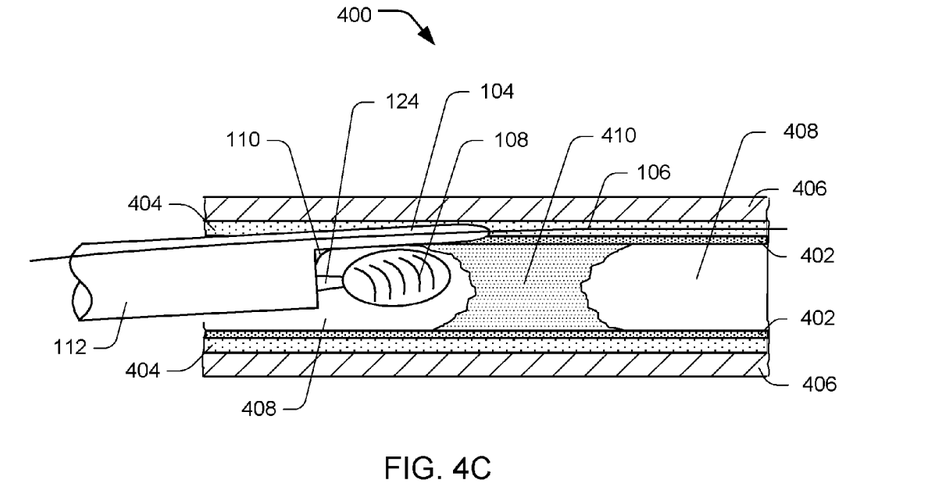

The guide member 104 may be adapted to facilitate further dissection of tissue layers of the blood vessel, if desired. For example, the distal tip of the guide member 104 may be sufficiently rigid and/or made with a blunt tip to dissect tissue layers as guide member 104 tracks along the guidewire 106. The distal movement of the recanalization catheter assembly may advance the guide member 104 out of the lumen 408 into the subintimal space between the intimal layer 402 and the adventitial layer 406, as shown in FIG. 4C, where rotary ablation tool 108 approaches the occlusion 410 in the lumen 408.

The cutter 110, which may be located between the guide member 104 and the rotary ablation tool 108, may be used to dissect or cut through tissue, such as the intimal layer 402, or a portion thereof, located between the guide member 104 (in the subintimal space) and the rotary ablation tool 108 (in the lumen 408). In another embodiment, the guide member 104 and the cutter 110 may be advanced distally in the subintimal space over the guidewire 106 prior to advancing the catheter sub-unit in the true lumen 408 of the blood vessel such that a distal end of the catheter sub-unit subsequently meets a proximal end of the guide member 104. In yet another embodiment, the guide member 104 may be advanced distally in the subintimal space over the guidewire 106, followed by the distal end of the catheter sub-unit, as well as the cutter 110, to subsequently meet the proximal end of the guide member 104.

Figure 4D:
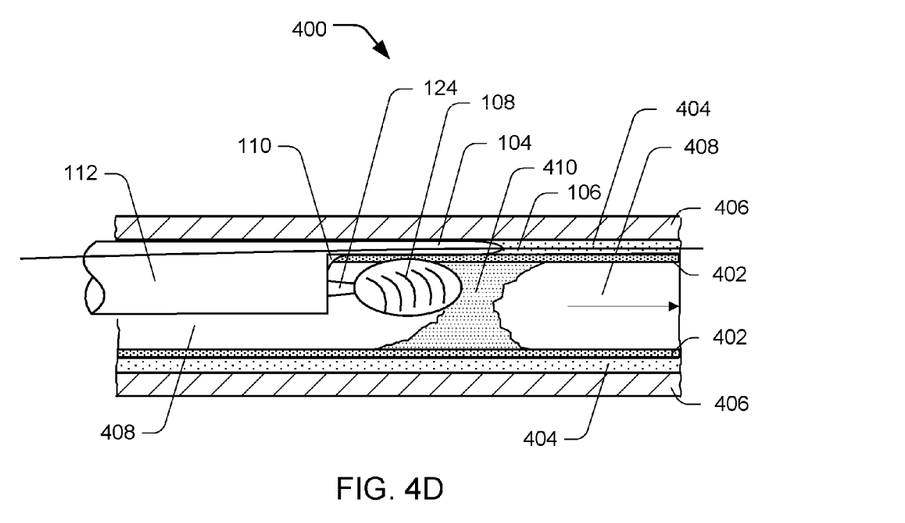

As shown in FIG. 4D, further distal movement of recanalization catheter assembly 100 may advance the rotary ablation tool 108 into engagement with occlusion 410. The spacing between the guide member 104 and rotary ablation tool 108 may allow the guide member 104 to advance through the subintimal space while the rotary ablation tool 108 is located in lumen 408 to encounter the occlusion 410. The guide member 104 may help guide the rotary ablation tool 108 through the occlusion 410, and thus help prevent the rotary ablation tool 108 from deviating from a path through the occlusion. The rotary ablation tool 108, which may be driven by motor 118 via flexible shaft 124, may penetrate through the occlusion 410 from its proximal end to create or enlarge a passage through the occlusion 410. In other embodiments, a different ablation device, such as an electrosurgical (e.g., radio frequency) ablation device, ultrasonic ablation device, laser ablation device, or other ablation device may be used to create or enlarge a passage through the occlusion 410. Once the passage has been created across the occlusion 410, the recanalization catheter assembly 100 may be withdrawn and one or more medical devices, such as an inflatable balloon and a stent, may be advanced through the passage in the blood vessel to enlarge the passage and/or pass distally of the occlusion 410 to perform a further medical procedure.

Those skilled in the art will recognize the aspects of the present disclosure may be manifest in a variety of forms other than the specific embodiments described and contemplated herein. Accordingly, departure in form and detail may be made without departing from the scope and spirit of the present disclosure as described in the appended claims.

What is claimed is:

1. A recanalization catheter assembly for recanalizing a blood vessel having an occlusion in a lumen thereof, the catheter assembly comprising:
    an elongate shaft including a tubular portion having a lumen, a distal opening, and a guide member fixed to and extending distal of the distal opening, the guide member including a guidewire lumen for receiving a guidewire therethrough;
    a rotary ablation tool extending distally from the distal opening alongside the guide member; and
    a cutting member between the guide member and the rotary ablation tool, the cutting member located proximal of the rotary ablation tool;
    wherein the guide member is configured to be advanced over a guidewire in a subintimal space between a first tissue layer and a second tissue layer of a wall of the blood vessel, while the rotary ablation tool is advanced in the lumen of the blood vessel to ablate the occlusion,
    wherein the cutting member is configured to cut through the first tissue layer between the guide member and the rotary ablation tool as the rotary ablation tool is advanced distally through the occlusion,
    wherein the rotary ablation tool includes a drive shaft rotatably extending through the lumen of the elongate shaft.

2. The recanalization catheter assembly of claim 1, wherein the cutting member is a stationary member having a sharp edge.

3. The recanalization catheter assembly of claim 1, wherein the cutting member is located proximate the distal opening.

4. The recanalization catheter assembly of claim 1, wherein the guidewire lumen extends into tubular portion of the elongate shaft proximal of the guide member.

5. The recanalization catheter assembly of claim 1, wherein a distal end of the guide member extends distal of a distal end of the rotary ablation tool.

6. The recanalization catheter assembly of claim 1, wherein the guidewire lumen extends proximal of the guide member through at least a portion of the elongate shaft.

7. The recanalization catheter assembly of claim 1, wherein the guide member is configured to guide the rotary ablation tool through the occlusion as the guide member is advanced over the guidewire positioned in the subintimal space.

8. A method of recanalizing a blood vessel having an occlusion in a lumen thereof, the method comprising:
    advancing a guidewire out of a lumen of a blood vessel into a wall of the blood vessel between a first tissue layer and a second tissue layer to form a subintimal space;
    advancing the recanalization catheter assembly of claim 1 over the guidewire;
    advancing the guide member over the guidewire in the subintimal space between the first tissue layer and the second tissue layer; and
    advancing the rotary ablation tool in the lumen of the blood vessel and through the occlusion while the guide member is advanced over the guidewire positioned in the subintimal space to ablate the occlusion.

9. The method of claim 8, further comprising:
    cutting through the first tissue layer between the guide member and the rotary ablation tool with the cutter member as the rotary ablation tool is advanced distally through the occlusion.

10. The method of claim 8, wherein the cutting member is positioned proximate the distal opening of the tubular portion of the elongate shaft.

11. The method of claim 8, wherein a distal end of the guidewire remains in the subintimal space while advancing the rotary ablation tool through the occlusion.

12. The method of claim 8, wherein the distal opening of the elongate shaft remains in the lumen of the blood vessel while the guide member is advanced through the subintimal space over the guidewire.

13. A recanalization catheter assembly for recanalizing a blood vessel having an occlusion in a lumen thereof, the catheter assembly comprising:
    an elongate shaft including a tubular portion having a first lumen extending therethrough to a distal opening, a guide member fixed to and extending distal of the distal opening, and a guidewire lumen extending through the guide member for receiving a guidewire therethrough;
    a rotary ablation tool including a elongate drive shaft rotatably extending through the first lumen to a rotatable cutter extending distally from the distal opening alongside the guide member; and
    a stationary cutting member secured to the elongate shaft proximal of the rotatable cutter and distal to the distal opening;
    wherein the guide member is configured to be advanced over a guidewire in a subintimal space between a first tissue layer and a second tissue layer of a wall of the blood vessel, while the rotary ablation tool is advanced in the lumen of the blood vessel to ablate the occlusion; and
    wherein the cutting member is configured to cut through the first tissue layer between the guide member and the rotary ablation tool as the rotary ablation tool is advanced distally through the occlusion.

14. The recanalization catheter assembly of claim 13, wherein the guide member is configured to guide the rotary ablation tool through the occlusion as the guide member is advanced over the guidewire positioned in the subintimal space.

15. The recanalization catheter assembly of claim 13, wherein the cutting member is a stationary member having a sharp edge.

16. The recanalization catheter assembly of claim 13, wherein a distal end of the guide member extends distal of a distal end of the rotatable cutter.

17. The recanalization catheter assembly of claim 13, wherein the cutting member is located proximate the distal opening.

* * * * *